US009921208B2

(12) United States Patent
Gofman (10) Patent No.: US 9,921,208 B2
(45) Date of Patent: Mar. 20, 2018

(54) APPARATUS AND METHODS FOR REDUCING ELECTRICAL SHOCK HAZARD FROM BIOSENSOR METERS

(71) Applicant: Bayer Healthcare LLC, Whippany, NJ (US)

(72) Inventor: Igor Gofman, Croton-on-Hudson, NY (US)

(73) Assignee: Ascensia Diabetes Care Holdings AG, Basel (CH)

( * ) Notice: Subject to any disclaimer, the term of this patent is extended or adjusted under 35 U.S.C. 154(b) by 127 days.

(21) Appl. No.: 14/411,489

(22) PCT Filed: Mar. 5, 2013

(86) PCT No.: PCT/US2013/028983
§ 371 (c)(1),
(2) Date: Dec. 26, 2014

(87) PCT Pub. No.: WO2014/018097
PCT Pub. Date: Jan. 30, 2014

(65) Prior Publication Data
US 2015/0160187 A1    Jun. 11, 2015

Related U.S. Application Data

(60) Provisional application No. 61/675,953, filed on Jul. 26, 2012.

(51) Int. Cl.
*G01N 33/49*    (2006.01)
*G01N 33/487*   (2006.01)

(52) U.S. Cl.
CPC .  *G01N 33/48785* (2013.01); *G01N 33/48792* (2013.01); *G01N 33/49* (2013.01); *Y10T 436/144444* (2015.01)

(58) Field of Classification Search
CPC ........... G01N 33/48785; G01N 33/487; G01N 33/483; G01N 33/48; G01N 33/49;
(Continued)

(56) References Cited

U.S. PATENT DOCUMENTS 7,435,384 B2   10/2008   Fish
7,514,040 B2    4/2009   Wu et al.
(Continued)

FOREIGN PATENT DOCUMENTS

CN    1322949 A   11/2001
CN    2694271 Y    4/2005
(Continued)

OTHER PUBLICATIONS

Chinese Search Report of Chinese Application No. 201380038446.7, dated Feb. 2, 2016.
(Continued)

*Primary Examiner* — Christine T Mui
(74) *Attorney, Agent, or Firm* — Dugan & Dugan, PC (57) ABSTRACT

A biosensor meter (10a) is provided for determining an analyte concentration in a fluid, such as glucose in blood. The biosensor meter includes a USB port (14a) having a first data signal port terminal (32d'), and a detection circuit (50a) including a first input terminal and an output terminal. The first input terminal of the detection circuit (50a) is coupled to the first data signal port terminal (32d'). The detection circuit (50a) provides at the output terminal a first output signal when a current sensed at the first input terminal is greater than or equal to a first predetermined amount, and a second output signal when the current sensed at the first input terminal is less than the first predetermined amount. The detection circuit is configured to detect whether the USB port (14a) of the biosensor meter (10a) is connected to the USB port (14b) of another electronic device, such as a
(Continued)

computer (12), and to prompt the meter's user for not carrying out a measurement in order to reduce the risk of electrical shock.

32 Claims, 5 Drawing Sheets

(58) Field of Classification Search
CPC ... Y10T 436/14444; Y10T 436/143333; Y10T 436/142222; Y10T 436/141111; Y10T 436/14
USPC ..... 436/95, 94, 93, 91, 150, 149; 422/82.02, 422/82.01, 68.1, 50
See application file for complete search history.

(56) References Cited

U.S. PATENT DOCUMENTS

| | | | |
|---|---|---|---|
| 2006/0025663 A1* | 2/2006 | Talbot | A61B 5/0002 600/365 |
| 2007/0084734 A1* | 4/2007 | Roberts | G01N 27/3274 205/792 |
| 2008/0114228 A1 | 5/2008 | McCluskey et al. | |
| 2009/0127135 A1 | 5/2009 | Huang | |
| 2011/0093286 A1* | 4/2011 | Dicks | A61B 5/0022 705/2 |
| 2011/0137571 A1 | 6/2011 | Power et al. | |
| 2011/0244699 A1 | 10/2011 | Bernstein et al. | |
| 2011/0296158 A1 | 12/2011 | Elder | |
| 2012/0067743 A1 | 3/2012 | Lin | |

FOREIGN PATENT DOCUMENTS

| | | | | |
|---|---|---|---|---|
| CN | 101689227 A | | 3/2010 | |
| CN | 201453279 U | | 5/2010 | |
| CN | 101762707 A | | 6/2010 | |
| CN | 102046080 A | | 5/2011 | |
| EP | 2 273 400 | | 1/2011 | |
| JP | 2007-114197 | | 5/2007 | |
| JP | 2009-532706 | | 9/2009 | |
| JP | 2010-181219 | | 8/2010 | |
| JP | 2012-509698 | | 4/2012 | |
| RU | 68714 U1 | | 11/2007 | |
| RU | 79344 U1 | | 12/2008 | |
| RU | 2450257 C1 | | 5/2012 | |
| WO | WO 2009/059194 | * | 5/2009 | ............... A61B 5/00 |
| WO | WO 2009/059203 | | 5/2009 | |
| WO | WO 2011/148142 | | 12/2011 | |
| WO | WO 2012/049221 | | 4/2012 | |

OTHER PUBLICATIONS

Taiwan Search Report of Taiwan Application No. 102109108, dated Apr. 19, 2016.
International Search Report and Written Opinion of International Application No. PCT/US13/28983, dated Jun. 17, 2013.
International Preliminary Report on Patentability and Written Opinion of International Application No. PCT/US13/28983, dated Feb. 5, 2015.
Russian Search Report of Russian Application No. 2015106361, dated Feb. 20, 2017.
Japanese Office Action of Japanese Application No. 2015-524246, dated Jan. 30, 2017.

* cited by examiner

APPARATUS AND METHODS FOR REDUCING ELECTRICAL SHOCK HAZARD FROM BIOSENSOR METERS

CROSS-REFERENCE TO RELATED APPLICATIONS

This application claims the benefit of U.S. Provisional Patent Application Ser. No. 61/675,953, filed Jul. 26, 2012, titled "APPARATUS AND METHODS FOR REDUCING ELECTRICAL SHOCK HAZARD FROM BIOSENSOR METERS," which is incorporated by reference herein in its entirety for all purposes.

BACKGROUND

This invention relates to biosensor meters, such as blood glucose monitors, used to detect or monitor an analyte, such as glucose, in a fluid sample, such as blood. In particular, this invention relates to apparatus and methods for reducing electrical shock hazard from biosensor meters.

SUMMARY

In a first aspect of the invention, a biosensor meter is provided for determining an analyte concentration in a fluid. The biosensor meter includes a USB port having a first data signal port terminal, and a detection circuit including a first input terminal and an output terminal. The first input terminal of the detection circuit is coupled to the first data signal port terminal. The detection circuit provides at the output terminal a first output signal when a current sensed at the first input terminal is greater than or equal to a first predetermined amount, and a second output signal when the current sensed at the first input terminal is less than the first predetermined amount.

In a second aspect of the invention, a method is provided for use with a biosensor meter used to determine an analyte concentration in a fluid. The biosensor meter includes a USB port having a first data signal port terminal. The method includes providing a detection circuit including a first input terminal and an output terminal, the first input terminal coupled to the first data signal port terminal. The method also includes providing a first output signal at the output terminal when a current sensed at the first input terminal is greater than or equal to a first predetermined amount, and providing a second output signal at the output terminal when the current sensed at the first input terminal is less than the first predetermined amount.

Other features and aspects of the present invention will become more fully apparent from the following detailed description, the appended claims and the accompanying drawings.

BRIEF DESCRIPTION OF THE DRAWINGS

Features of the present invention can be more clearly understood from the following detailed description considered in conjunction with the following drawings, in which the same reference numerals denote the same elements throughout, and in which.

DETAILED DESCRIPTION

Apparatus and methods in accordance with this invention determine if a biosensor meter is connected to a USB port of a computer device (e.g., a USB port of a personal computer), and if a USB port connection is detected, disable fluid sample analysis. In particular, biosensor meters in accordance with this invention determine if the biosensor meter is connected to a USB port of computer device regardless of whether the computer device is ON or OFF, and regardless of whether the computer device is functioning normally or not. As described in more detail below, if the biosensor meter determines that the meter is connected to a USB port of a computer device, the biosensor meter disables fluid sample analysis.

Biosensor meters are commonly used to detect or monitor analytes in bodily fluids, such as blood, urine or other bodily fluids. Many biosensor meters are configured for use with analytical test strips that are used to collect a sample of a user's bodily fluid. In particular, a user collects a fluid sample on a test strip, and then inserts the test strip into a port in the biosensor meter. The meter analyzes the fluid sample and then reports analysis results.

For example, a blood glucose meter ("BGM") is a biosensor meter used to measure glucose levels in a sample of a user's blood. For some BGM devices, a user inserts a test strip into the BGM, and the BGM displays a message inviting the user to apply blood to the test strip. After the user applies the blood sample, the BGM analyzes the blood sample to determine the blood glucose level in the sample, and reports the results to the user (e.g., via a display and/or a speaker).

For enhanced data storage and analysis, many biosensor meters include an interface to couple the meter to a personal computer ("PC"). Indeed, some biosensor meters include a USB port that may be plugged into a USB port on a PC, which may include software that extracts, stores and analyzes data from the biosensor meter. For example, the CONTOUR® USB Blood Glucose Meter by Bayer Healthcare, Tarrytown, N.Y., may be plugged into a PC to access historical blood sugar data and trends to help optimize diabetes management. Biosensor meters that include USB ports will be referred to herein as "USB biosensor meters."

Biosensor meters are typically battery-powered, lightweight, handheld devices. Because of the low supply voltage provided by the batteries, biosensor meters generally are not electrically hazardous. USB biosensor meters, however, have the potential for causing electrical hazards when the devices are coupled to a personal computer.

Figure 1:
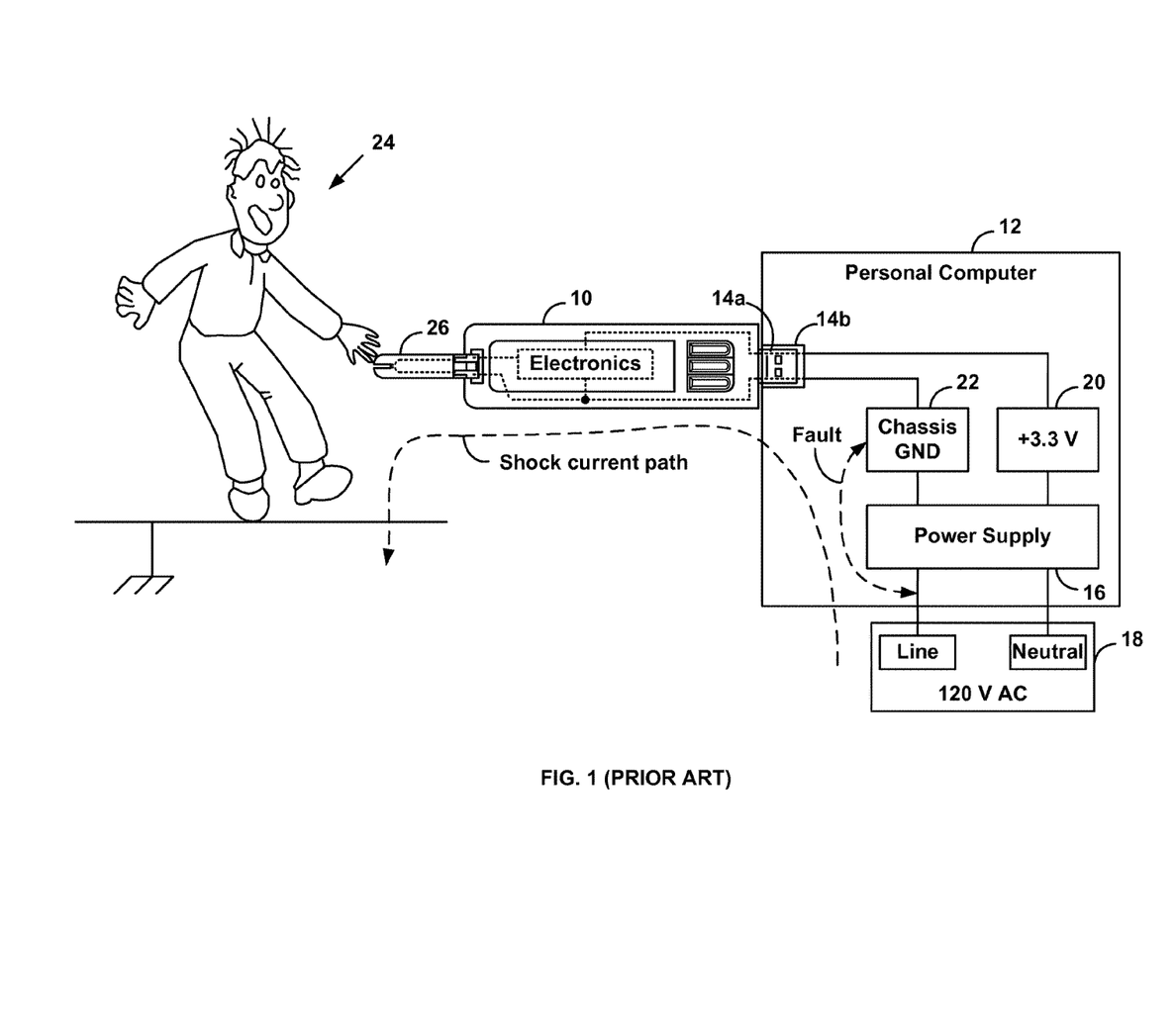
FIG. 1 is a diagram of a previously known biosensor meter coupled via a USB port to a personal computer.

For example, FIG. 1 illustrates a USB biosensor meter (e.g., a BGM) 10 coupled to a PC 12. In particular, USB biosensor meter 10 includes a USB port 14a coupled to USB port 14b of PC 12. PC 12 includes a power supply 16 that is coupled to external AC voltage source 18 (e.g., an electrical outlet that includes LINE (hot) and NEUTRAL voltages), and that provides DC outputs 20 (e.g., +3.3V) and 22 (e.g., Chassis GND) to internal circuitry in personal computer 12, including electrical conductors in USB port 14b.

If power supply 16 fails (e.g., an internal short circuit occurs), and the LINE signal becomes coupled to Chassis GND, the internal circuitry in PC 12 is no longer isolated from the LINE voltage. This can occur even if PC 12 is OFF. Such a scenario is unlikely to be problematic if personal computer 12 is a desktop PC, because desktop PCs are typically grounded via a three-prong electrical plug. In such instances, if a fault occurs in power supply 16, an internal fuse in PC 12 will blow, and the LINE voltage will be disconnected from the internal circuitry.

If PC 12 is a desktop PC that is not properly grounded, however, or if PC 12 is a laptop computer connected via an external power adapter to an electrical outlet via an ungrounded two-prong plug, a failure of power supply 16 may cause the internal circuitry of PC 12 to be coupled to the LINE signal, with no external grounding protection for the internal circuitry.

As a result, if USB biosensor meter 10 is coupled to PC 12 with a faulty power supply 16, electrical conductors in USB biosensor meter 10 may be coupled via USB port 14a to LINE voltage. If a user 24 inserts a test strip 26 into USB biosensor meter 10, and touches test strip 26 to provide a fluid sample, an electrical shock current path may form as shown in FIG. 1.

USB biosensor meters typically include instructions that warn a user not to perform testing while the meter is connected to a PC via the USB port. However, not all users read documentation, and even those users who read the documentation may eventually forget about the warnings after some time has elapsed. In addition, because USB biosensor meters are typically small devices, conventional protection methods related to electrical or mechanical circuit separation are almost impossible. Thus, existing USB biosensor meters pose a potential shock risk to users.

Apparatus and methods in accordance with this invention determine if a USB biosensor meter is connected to a USB port of a PC, and if a USB port connection is detected, disable fluid sample analysis. In particular, USB biosensor meters in accordance with this invention determine if the USB biosensor meter is connected to a USB port of a PC, regardless of whether the PC is ON or OFF, and regardless of whether the PC is functioning normally or not. As described in more detail below, if the USB biosensor meter determines that the meter is connected to a USB port of a PC, USB biosensor meters in accordance with this invention disable fluid sample analysis.

For example, USB biosensor meters in accordance with this invention may include a display that displays a message warning the user to not apply a fluid sample to the test strip, and/or to remove a test strip from the meter. In this regard, the user never receives the invitation to apply fluid to the test strip, and thus reduces the risk of electrical shock to the user.

In addition, or alternatively, USB biosensor meters in accordance with this invention may include a speaker that may sound an audible alarm, beep, or spoken message warning the user not to apply a fluid sample to test strip. In addition, or alternatively, USB biosensor meters in accordance with this invention may vibrate to warn a user not to apply a fluid sample to the test strip, and/or may eject the test strip from the meter to prevent the user from applying a fluid sample to the test strip.

Figure 2A:
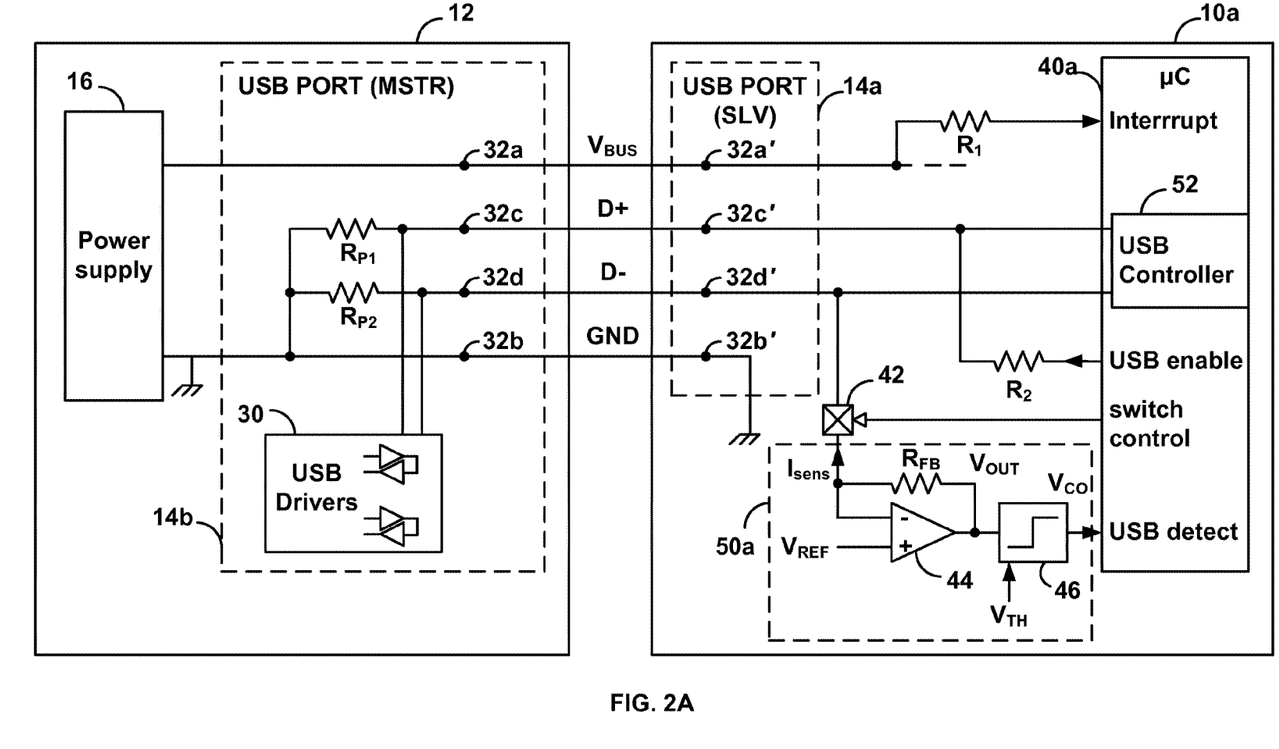
FIG. 2A is a diagram of an example biosensor meter in accordance with this invention coupled to a personal computer.

Referring now to FIG. 2A, a system including a first example USB biosensor meter 10a in accordance with this invention is described. In this example embodiment, USB biosensor meter 10a includes USB slave port 14a coupled to USB master port 14b of PC 12. PC 12 may be a desktop computer, mainframe, computer server, laptop computer, tablet computer, wireless telephone, smartphone, or other similar computer device. In the illustrated examples described below, a +3.3V supply voltage is assumed. Persons of ordinary skill in the art will understand that methods and apparatus in accordance with this invention also may use other supply voltages.

USB master port 14b is a conventional USB master port that includes USB master port resistors $R_{P1}$ and $R_{P2}$ and USB drivers 30, and provides power bus signals ($V_{BUS}$ and GND) and data signals (D+ and D−) at port terminals 32a, 32b, 32c and 32d, respectively. In accordance with USB standards, USB master port resistors $RP_{P1}$ and $R_{P2}$ each may have values between 14.25 kΩ and 24.8 kΩ, and are connected between port terminals 32c (D+) and 32d (D−), respectively, and port terminal 32b (GND). Also in accordance with USB standards, data lines D+ and D− are inactive until a peripheral device enables USB operation by providing a voltage from +3.0V to +3.3V to data signals D+ or D− via a resistor having a value between 900Ω and 1575Ω.

USB biosensor meter 10a includes USB slave port 14a, a microcontroller 40a, a controlled switch 42, an operational amplifier ("opamp") 44, a comparator 46, a first resistor $R_1$, a second resistor $R_2$, a feedback resistor $R_{FB}$, a voltage reference $V_{REF}$, and a threshold voltage $V_{TH}$. USB slave port 14a includes port terminals 32a', 32b', 32c' and 32d', that correspond to port terminals 32a, 32b, 32c and 32d, respectively, of USB master port 14b. Persons of ordinary skill in the art will understand that USB biosensor meters in accordance with this invention may include components other than or in addition to the ones shown in FIG. 2A.

Microcontroller 40a may be a conventional microcontroller, such as the ARM Cortex™-M3 processor, by ARM Holdings, Cambridge, UK, or other similar microcontroller. Microcontroller 40a includes an interrupt input coupled to port terminal 32a' ($V_{BUS}$) via first resistor $R_1$, a USB slave controller 52 coupled to port terminals 32c' (D+) and 32d' (D−), a USB enable output coupled to port terminal 32c' (D+) via second resistor $R_2$, a switch control output coupled to a control input of controlled switch 42, and a USB detect input coupled to an output $V_{CO}$ of comparator 46. Persons of ordinary skill in the art will understand that microcontroller 40a typically may include inputs and outputs in addition to or different from the ones depicted in FIG. 2A.

First resistor $R_1$ may be a 10 kΩ±1-5% resistor, although other resistor values may be used, and second resistor $R_2$ may have a value between 900Ω and 1575Ω. Persons of ordinary skill in the art will understand that USB Enable output alternatively may be coupled to port terminal 32d' (D−) via second resistor $R_2$.

Controlled switch 42 has a first terminal coupled to an inverting input of opamp 44, and a second terminal coupled to port terminal 32d' (D−), and operates to connect or disconnect the inverting input of opamp 44 and port terminal 32d' (D−) based on the value of the switch control signal from microcontroller 40a. For example, if the switch control signal has a first value (e.g., "OFF" or 0V), the inverting input of opamp 44 may be disconnected from port terminal 32d' (D−). Alternatively, if the switch control signal has a second value (e.g., "ON" or +3.3V), the inverting input of opamp 44 may be connected to port terminal 32d' (D−).

Controlled switch 42 may be a general purpose IC switch, such as the NX3L1T66 low-ohmic single-pole single-throw analog switch by NXP Semiconductors, Eindhoven, The Netherlands, or other similar switch. Persons of ordinary skill in the art will understand that the switching convention described above may be inverted, and also will understand that the inverting input of opamp 44 alternatively may be switchably connected to port terminal 32c' (D+).

Opamp 44 has a non-inverting input coupled to voltage reference signal $V_{REF}$, an inverting input coupled to a first terminal of feedback resistor $R_{FB}$, and an output $V_{OUT}$ coupled to a second terminal of feedback resistor $R_{FB}$. Opamp 44 may be a general purpose opamp, such as the MCP6001T opamp by Microchip Technology Inc., Chandler, Ariz. or other similar opamp.

Feedback resistor $R_{FB}$ may be a 140 kΩ resistor. Voltage reference $V_{REF}$ may have a value of +0.25V, and threshold voltage $V_{TH}$ may have a value of +1.3V. As described in more detail below, however, other values may be used for feedback resistor $R_{FB}$, voltage reference $V_{REF}$, and threshold voltage $V_{TH}$.

Comparator 46 has a first input coupled to the output $V_{OUT}$ of opamp 44, a second input coupled to threshold voltage $V_{TH}$, and an output $V_{CO}$ coupled to the USB detect input of microcontroller 40a. Comparator 46 may be a general purpose comparator, such as the LT1713CMS8 comparator by Linear Technology Corporation, Milpitas, Calif., or other similar comparator.

In accordance with this invention, USB biosensor meter 10a is capable of determining if USB slave port 14a is coupled to USB master port 14b of PC 12, regardless of whether PC 12 is ON or OFF, and regardless of whether PC 12 is functioning normally or not.

Figure 3:
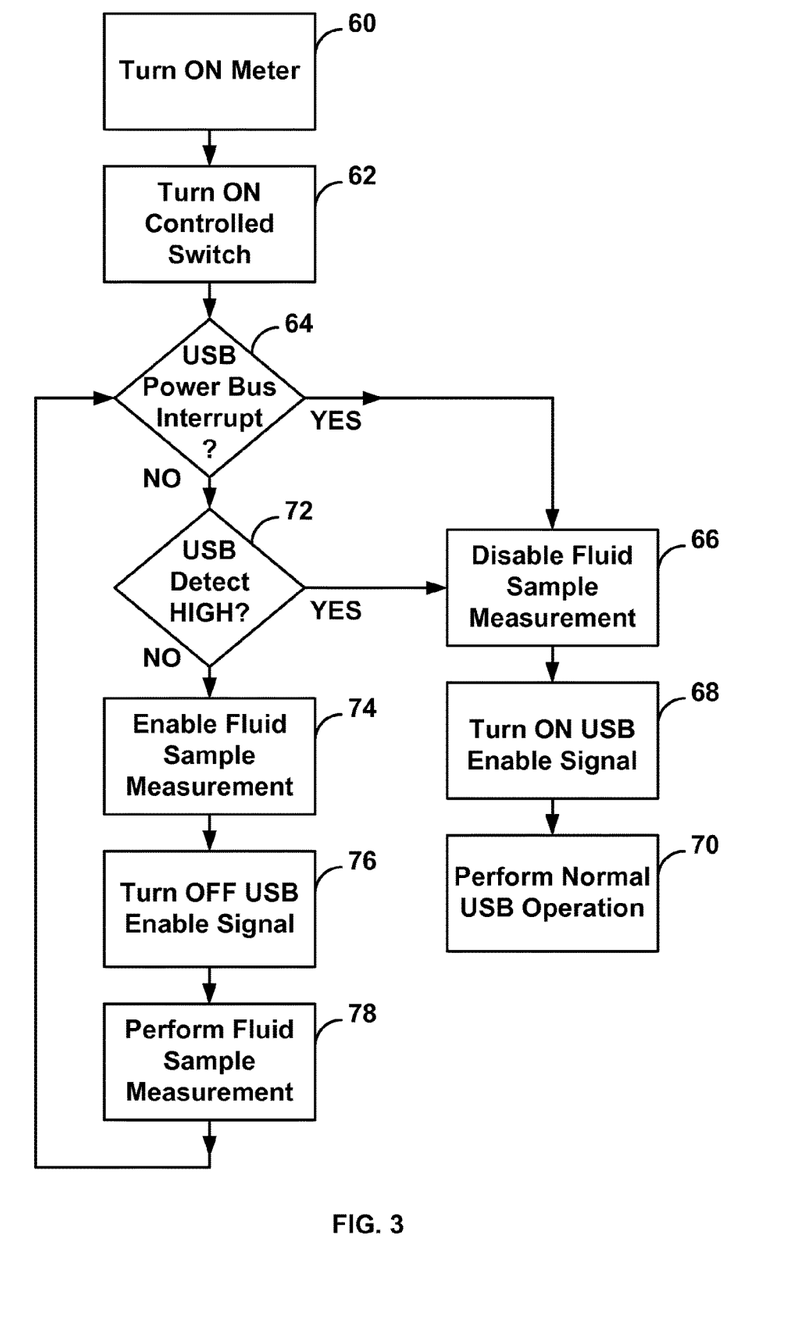
FIG. 3 is a flow chart of an example process in accordance with this invention.

Referring now to FIGS. 2A and 3, an example operation of USB biosensor meter 10a is described. At step 60, USB biosensor meter 10a is turned ON. For example, a user may activate a switch (not shown) on USB biosensor meter 10a to turn on the meter, or a user may insert a test strip into the meter, which may cause USB biosensor meter 10a to turn ON. Persons of ordinary skill in the art will understand that other techniques may be used to turn ON USB biosensor meter 10a.

At step 62, the switch control signal of microcontroller 40a turns ON controlled switch 42. At step 64, microcontroller 40a determines if a USB power bus interrupt has occurred. In particular, if PC 12 is turned ON and is functioning normally, USB power bus signal $V_{BUS}$ has a non-zero value (e.g., +3.3V for a system using a 3.3V supply). If USB slave port 14a is coupled to USB master port 14b of PC 12, the USB power bus signal $V_{BUS}$ is coupled via port terminals 32a and 32a' and first resistor 48 to the Interrupt input of microcontroller 40a. A non-zero value of USB power bus signal $V_{BUS}$ that is greater than the interrupt threshold (e.g., $V_{BUS}$>2.64V for a system using a 3.3V supply) of microcontroller 40a will thus trigger an interrupt in microcontroller 40a.

As a result of receiving this interrupt, microcontroller 40a determines that USB slave port 14a is coupled to USB master port 14b of PC 12. Accordingly, at step 66, to prevent potential shock injury to the user, USB biosensor meter 10a disables fluid sample measurement.

Figure 4A:
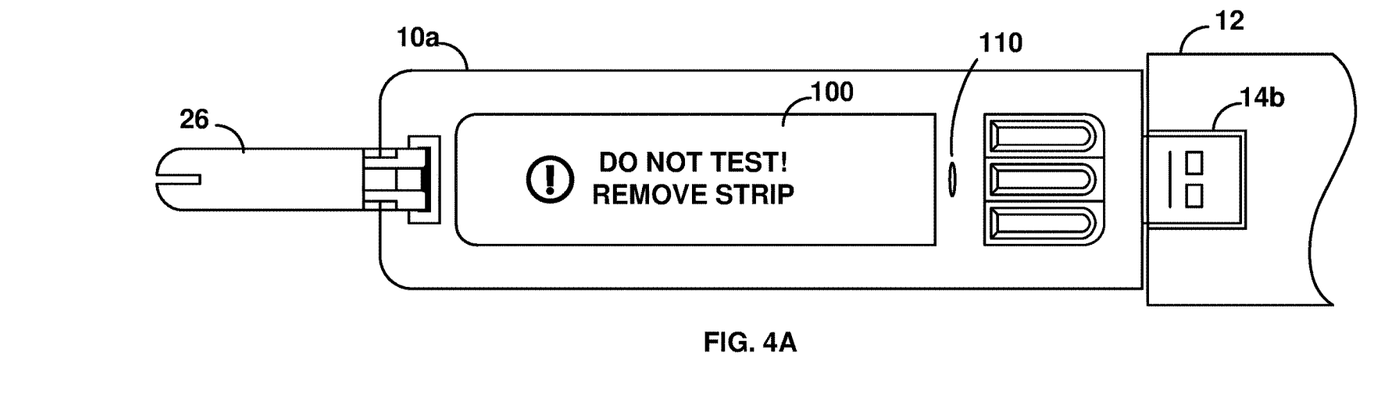
FIGS. 4A-4B are diagrams of example biosensor meters in accordance with this invention.

For example, as shown in FIG. 4A, USB biosensor meter 10a may include a display 100 (e.g., a liquid crystal display or other similar display) that displays a warning message, such as "DO NOT TEST! REMOVE STRIP," or other similar message that may warn the user not to apply a fluid sample to test strip 26.

Persons of ordinary skill in the art will understand that USB biosensor meter 10a may use other techniques to disable fluid sample measurement. For example, USB biosensor meter 10a may include a speaker 110 that may sound an audible alarm, beep, or spoken message warning the user not to apply a fluid sample to test strip 26. USB biosensor meter 10a also may vibrate to warn a user not to apply a fluid sample to test strip 26. In addition, or alternatively, USB biosensor meter 10a may eject test strip 26 to prevent the user from applying a fluid sample to test strip 26. Persons of ordinary skill in the art will understand that other similar techniques may be used to disable fluid sample measurement, and that one or more of these techniques may be combined.

Referring again to FIG. 3, at step 68, microcontroller 40a turns ON the USB Enable signal (e.g., provides a +3.0V to +3.3V signal at the USB enable output) to activate data lines D+ and D−. In addition, microcontroller 40a may turn OFF the switch control signal (e.g., provide a 0V signal at the switch control output) to turn OFF controlled switch 42 and disconnect the inverting input of opamp 44 from port terminal 32d' (D−). At step 70, USB biosensor meter 10a performs a normal USB operation with PC 12 (e.g., exchanging data with PC 12, and/or other similar operations).

As described above, USB biosensor meters in accordance with this invention also are capable of determining if the meter is coupled to a USB port of PC 12 even if the PC is OFF or not functioning normally. Referring again to FIG. 2A, if PC 12 is turned OFF or is not functioning normally, the status of USB power bus signal $V_{BUS}$ may not reliably indicate whether USB slave port 14a is coupled to USB master port 14b of PC 12.

For example, if PC 12 is turned OFF or is not functioning normally, USB power bus signal $V_{BUS}$ may have some value (e.g., 0V, or noise) below the interrupt threshold of microcontroller 40a. In such circumstance, referring again to FIG. 3, at step 64 microcontroller 40a does not receive a USB power bus interrupt, and the process proceeds to step 72, to determine if the USB Detect input of microcontroller 40a is HIGH.

As mentioned above, referring again to FIG. 2A, when USB biosensor meter 10a turns ON, the switch control signal turns ON controlled switch 42. As a result, controlled switch 42 connects the inverting input of opamp 44 to port terminal 32d' (D−). If USB slave port 14a is coupled to USB master port 14b, a current $I_{sens}$ will flow from the inverting input of opamp 44 to USB master port resistor $R_{P2}$.

In this configuration, the output $V_{OUT}$ of opamp 44 is:

$$V_{OUT} = V_{REF}\left(1 + \frac{R_{FB}}{R_{P2}}\right) \quad (1)$$

and comparator 46 output $V_{CO}$ is:

$$V_{CO} = \begin{cases} \text{HIGH} & \text{if } V_{OUT} > V_{TH} \\ \text{LOW} & \text{if } V_{OUT} \leq V_{TH} \end{cases} \quad (2)$$

For example, if $V_{REF}$ is +0.25V, $V_{TH}$ is +1.3V, $R_{FB}$=140 k and $R_{P2}$=(14.25 kΩ–24.8 kΩ), $V_{OUT}$=(2.46V–1.41V)>$V_{TH}$, and thus the comparator 46 output $V_{CO}$ will be HIGH (e.g., +3.3V). As a result, the USB detect input value is HIGH, which indicates that USB slave port 14a is coupled to USB master port 14b. Accordingly, at step 72, microcontroller 40a detects the HIGH signal at the USB detect signal, and the process proceeds to steps 66-70, as described above, to disable fluid sample measurement.

Referring again to FIG. 2A, persons of ordinary skill in the art will understand that other $V_{REF}$, $V_{TH}$ and $R_{FB}$ values may be used in accordance with equations (1) and (2), above. For example, feedback resistor $R_{FB}$ may be determined using the following equation:

$$R_{FB} > \left(\frac{V_{TH} - V_{REF}}{V_{REF}}\right) R_{P2(max)} \quad (3)$$

where $R_{P2(max)}$=24.8 k. Thus, if $V_{TH}$=1.5V and $V_{REF}$=0.1V, $R_{FB}$>347.2 kΩ.

If USB slave port 14a is not coupled to USB master port 14b, no current $I_{sens}$ will flow from the inverting input of opamp 44 to USB master port resistor $R_{P2}$. In this configuration, output $V_{OUT}$ of opamp 44 equals the value of voltage reference $V_{REF}$. For example, if $V_{REF}$ is +0.25V and $V_{TH}$ is +1.3V, $V_{OUT}$=$V_{REF}$=+0.25<$V_{TH}$, and comparator 46 output $V_{CO}$ will be LOW (e.g., 0V). As a result, the USB detect input value is LOW.

Accordingly, referring again to FIG. 3, at step 72, microcontroller 40a does not detect the HIGH signal at the USB detect signal. Thus, microcontroller 40a determines that USB biosensor meter 10a is not coupled to PC 12. Accordingly, at step 74, USB biosensor meter 10a enables fluid sample measurement.

Figure 4B:
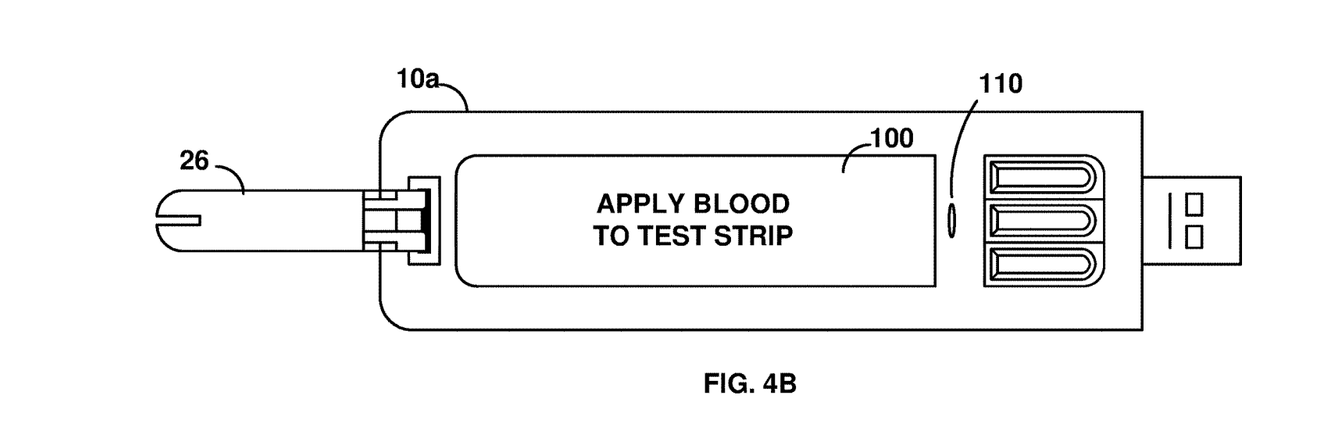

For example, as shown in FIG. 4B, display 100 of USB biosensor meter 10a may display a invitation message, such as "APPLY BLOOD TO TEST STRIP," or other similar message to invite the user to apply a fluid sample to test strip 26. Persons of ordinary skill in the art will understand that USB biosensor meter 10a may use other techniques to invite the user to apply a fluid sample to test strip 26. For example, USB biosensor meter 10a may include a speaker 110 that may sound a message inviting the user to apply a fluid sample to test strip 26. Persons of ordinary skill in the art will understand that other similar techniques may be used to invite a user to apply a fluid sample to test strip 26, and that one or more of these techniques may be combined.

Referring again to FIG. 3, at step 76, microcontroller 40a turns OFF the USB Enable signal (e.g., provides a 0V signal at the USB enable output) to thereby not activate data lines D+ and D−. At step 78, USB biosensor meter 10a performs a normal fluid sample measurement (e.g., analyzing the sample and displaying and/or announcing the analysis results). After performing the fluid sample analysis, the process may return to step 64 to determine if the user has connected USB slave port 14a of USB biosensor meter 10a to USB master port 14b of PC 12. Alternatively, USB biosensor meter 10a may turn OFF, or may perform some other process steps.

In the embodiment of FIG. 2A, opamp 44, voltage reference $V_{REF}$, feedback resistor $R_{FB}$, threshold voltage $V_{TH}$ and comparator 46 form a detection circuit 50a including a first input terminal (the inverting input of opamp 44) and an output terminal (the output of comparator 46). The first input terminal of detection circuit 50a is coupled to a first data signal port terminal 32d' (D−). Detection circuit 50a provides at the output terminal a first output signal ($V_{CO}$=HIGH) when a current $I_{sens}$ sensed at the first input terminal is greater than or equal to a first predetermined amount ($V_{TH}/R_{P1}$), and a second output signal ($V_{CO}$=LOW) when the current $I_{sens}$ sensed at the first input terminal is less than the first predetermined amount ($V_{TH}/R_{P1}$).

Figure 2B:
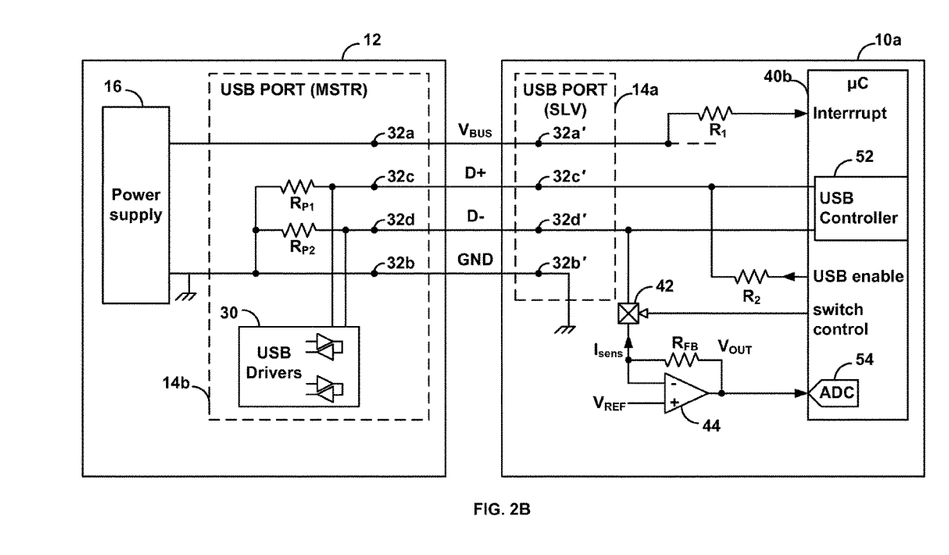
FIG. 2B is a diagram of another example biosensor meter in accordance with this invention coupled to a personal computer.

Referring now to FIG. 2B, an alternative example USB biosensor meter 10b in accordance with this invention is described. USB biosensor meter 10b is similar to USB biosensor meter 10a, but does not include comparator 46 or threshold voltage $V_{TH}$. In addition, USB biosensor meter 10b includes microcontroller 40b, which includes an analog-to-digital converter ("ADC") 54 having an input coupled to output $V_{OUT}$ of opamp 44. Microcontroller 40b may be a MSP430™ Ultra-Low Power 16-Bit Microcontrollers, by Texas Instruments, Dallas, Tex., or other similar microcontroller that includes an ADC.

In accordance with this invention, ADC 54 may convert output $V_{OUT}$ of opamp 44 to a digital value, and microcontroller 40b may then compare the digital output of ADC 54 to a digital value of threshold voltage $V_{TH}$ to determine if USB slave port 14a of USB biosensor meter 10b is coupled to USB master port 14b of PC 12. If the digital output of ADC 54 is greater than or equal to the digital value of threshold voltage $V_{TH}$, USB biosensor meter 10b may disable fluid sample measurement, as described above in connections with steps 66-70 of FIG. 3. If, however, the digital output of ADC 54 is less than the digital value of threshold voltage $V_{TH}$, USB biosensor meter 10b may enable fluid sample measurement, as described above in connections with steps 74-78 of FIG. 3.

The foregoing merely illustrates the principles of this invention, and various modifications can be made by persons of ordinary skill in the art without departing from the scope and spirit of this invention.

The invention claimed is:

1. A biosensor meter for determining an analyte concentration in a fluid, the biosensor meter comprising:
   a USB port comprising a first data signal port terminal; and
   a detection circuit for detecting a connection of the biosensor meter to a computer device, the detection circuit comprising a first input terminal coupled to the first data signal port terminal, and comprising an output terminal, wherein:
   the detection circuit is adapted to provide at the output terminal a first output signal when a current sensed at the first input terminal is greater than or equal to a first predetermined amount, and a second output signal when the current sensed at the first input terminal is less than the first predetermined amount,
   the biosensor meter is adapted to disable determination of the analyte concentration in the fluid when the detection circuit provides the first output signal at the output terminal, and
   the biosensor meter disables determination of the analyte concentration in the fluid by providing a warning to not apply a fluid sample to the biosensor meter.

2. The biosensor meter of claim 1, wherein the detection circuit comprises an operational amplifier comprising an inverting input coupled to first input terminal, and a non-inverting input coupled to a voltage reference.

3. The biosensor meter of claim 2, wherein the detection circuit further comprises a feedback resistor coupled between the inverting input and an output of the operational amplifier.

4. The biosensor meter of claim 1, further comprising a controlled switch coupled between the first input terminal and the first data signal port terminal.

5. The biosensor meter of claim 1, further comprising a microcontroller having an input terminal coupled to the output terminal of the detection circuit.

6. The biosensor meter of claim 1, wherein the warning comprises one or more of a displayed message and an audible sound.

7. The biosensor meter of claim 1, wherein the biosensor meter comprises a blood glucose monitor.

8. The biosensor meter of claim 1, wherein the detection circuit provides the first output signal at the output terminal when the USB port of the biosensor meter is coupled to a USB port of the computer device.

9. A method for use with a biosensor meter used to determine an analyte concentration in a fluid, the biosensor meter comprising a USB port comprising a first data signal port terminal, the method comprising:
providing a detection circuit for detecting a connection of the biosensor meter to a computer device, the detection circuit comprising a first input terminal coupled to the first data signal port terminal, and comprising an output terminal;
providing a first output signal at the output terminal when a current sensed at the first input terminal is greater than or equal to a first predetermined amount;
providing a second output signal at the output terminal when the current sensed at the first input terminal is less than the first predetermined amount; and
disabling determination of the analyte concentration in the fluid when the current sensed at the first input terminal is greater than or equal to a first predetermined amount, wherein the disabling comprises providing a warning to not apply a fluid sample to the biosensor meter.

10. The method of claim 9, further comprising providing a detection circuit that comprises an operational amplifier comprising an inverting input coupled to the first data signal port terminal, a non-inverting input coupled to a voltage reference, and an output that provides the first output signal and the second output signal.

11. The method of claim 10, further comprising providing a feedback resistor coupled between the inverting input and an output of the operational amplifier.

12. The method of claim 10, further comprising controllably switching the inverting input of the operational amplifier to the first data signal port terminal.

13. The method of claim 10, further comprising providing a microcontroller having an input terminal coupled to the output of the operational amplifier.

14. The method of claim 9, wherein the warning comprises one or more of a displayed message and an audible sound.

15. The method of claim 9, wherein the biosensor meter comprises a blood glucose monitor.

16. The method of claim 9, further comprising providing the first output signal when the USB port of the biosensor meter is coupled to a USB port of the computer device.

17. A biosensor meter comprising:
a fluid sample testing circuit;
a computer device connection port; and
a detection circuit coupled to the computer device connection port, wherein:
the biosensor meter is operative to disable the fluid sample testing circuit in response to the detection circuit detecting a connection between the computer device connection port and a computer device, and
the biosensor meter is further operative to provide a warning to not apply a fluid sample to the biosensor meter in response to the detection circuit detecting a connection between the computer device connection port and the computer device.

18. A biosensor meter for determining an analyte concentration in a fluid, the biosensor meter comprising:
a microcontroller;
a connection port coupled to the microcontroller; and
a detection circuit coupled to the connection port and to the microcontroller, the detection circuit operative to detect a connection at the connection port to a computer device that is OFF; wherein:
the microcontroller is operative to disable determination of the analyte concentration in the fluid in response to the detection circuit detecting the connection at the connection port to the computer device that is OFF.

19. The biosensor meter of claim 18, wherein the connection port comprises a USB port.

20. The biosensor meter of claim 18 further comprising a controlled switch having a first terminal coupled to the detection circuit and a second terminal coupled to the connection port, the controlled switch operative to connect or disconnect the detection circuit to and from the connection port in response to a control signal from the microcontroller.

21. The biosensor meter of claim 20, wherein the connection port comprises a first data signal port terminal coupled to the second terminal of the controlled switch and further comprises a power port terminal coupled to a power interrupt input of the microcontroller.

22. The biosensor meter of claim 18, wherein the microcontroller comprises:
a power interrupt input coupled to the connection port; and
a detect input coupled to an output of the detection circuit.

23. The biosensor meter of claim 18, wherein the detection circuit comprises:
an operational amplifier comprising an inverting input coupled to an input terminal of the detection circuit, and a non-inverting input coupled to a voltage reference; and
a comparator having an input coupled to an output of the operational amplifier and having an output coupled to the microcontroller.

24. The biosensor meter of claim 18, wherein the microcontroller comprises:
a power interrupt input coupled to the connection port; and
an analog-to-digital converter having an input.

25. The biosensor meter of claim 24, wherein the detection circuit comprises an operational amplifier comprising an inverting input coupled to an input terminal of the detection circuit, a non-inverting input coupled to a voltage reference, and an output coupled to the input of the analog-to-digital converter.

26. The biosensor meter of claim 18 further comprising a display operative to display a first message warning a user to not apply a fluid sample to a test strip and a second message inviting the user to apply a fluid sample to the test strip.

27. The biosensor meter of claim 18 further comprising a speaker operative to sound an audible alarm, beep, or spoken message warning a user to not apply a fluid sample to a test strip in response to the microcontroller disabling determination of the analyte concentration in the fluid.

28. A method of operating a biosensor meter comprising:
turning on the biosensor meter;
determining whether a power interrupt has occurred;
determining whether an output of a detection circuit in the biosensor meter is HIGH in response to not determining that a power interrupt has occurred;
disabling fluid sample measurement in the biosensor meter in response to determining that either the power interrupt has occurred or that the output of the detection circuit is HIGH; and enabling the fluid sample measurement in response to determining that no power interrupt has occurred and the output of the detection circuit is not HIGH.

29. The method of claim 28, wherein the disabling comprises displaying a warning message to not apply a fluid sample to a test strip, or activating an audible alarm, beep, or spoken message to not apply a fluid sample to the test strip.

30. The method of claim 28, wherein the enabling comprises displaying an invitation message to apply a fluid sample to a test strip.

31. The method of claim 28, further comprising:
turning ON a USB enable signal in response to determining that either the power bus interrupt has occurred or that the output of the detection circuit is HIGH; and
performing a USB operation.

32. The method of claim 28, further comprising:
turning OFF a USB enable signal in response to determining that no power interrupt has occurred and the output of the detection circuit is not HIGH; and
performing a fluid sample measurement.

\* \* \* \* \*